(12) United States Patent
Palla et al.

(10) Patent No.: US 9,945,767 B2
(45) Date of Patent: Apr. 17, 2018

(54) APPARATUS AND METHODS FOR DETERMINING SURFACE WETTING OF MATERIAL UNDER SUBTERRANEAN WELLBORE CONDITIONS

(71) Applicant: Halliburton Energy Services, Inc., Houston, TX (US)

(72) Inventors: Venkata Gopala Rao Palla, Pune (IN); Bhargav Gajji, Pune (IN); Sameer Bardapurkar, Pune (IN); Sairam KS Pindiprolu, Mumbai (IN)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/792,899

(22) Filed: Oct. 25, 2017

(65) Prior Publication Data

US 2018/0045633 A1 Feb. 15, 2018

Related U.S. Application Data

(62) Division of application No. 14/914,213, filed as application No. PCT/US2013/062035 on Sep. 26, 2013, now Pat. No. 9,829,421.

(51) Int. Cl.
| | |
|---|---|
| *G01R 27/28* | (2006.01) |
| *G01R 27/08* | (2006.01) |
| *G01V 3/00* | (2006.01) |
| *G01N 13/00* | (2006.01) |
| *E21B 21/00* | (2006.01) |
| *E21B 33/14* | (2006.01) |
| *E21B 41/00* | (2006.01) |
| *G01N 13/02* | (2006.01) |

(52) U.S. Cl.
CPC ............ *G01N 13/00* (2013.01); *E21B 21/00* (2013.01); *E21B 33/14* (2013.01); *E21B 41/00* (2013.01); *G01N 13/02* (2013.01); *G01N 2013/0225* (2013.01)

(58) Field of Classification Search
CPC ................................ G01V 3/00; G01V 27/08
USPC ........................................ 324/347, 649, 691
See application file for complete search history.

(56) References Cited

U.S. PATENT DOCUMENTS

| | | | |
|---|---|---|---|
| 4,557,142 A | 12/1985 | Hensley et al. | |
| H1932 H | * 1/2001 | Heathman | ............... 166/250.14 |
| 2002/0172341 A1 | 11/2002 | Jakoby et al. | |
| 2006/0070426 A1 | 4/2006 | Pelletier | |

(Continued)

OTHER PUBLICATIONS

International Search Report and Written Opinion issued in related PCT Application No. PCT/US2013/062035 dated Jun. 25, 2014, 9 pages.

(Continued)

*Primary Examiner* — Bot Ledynh
(74) *Attorney, Agent, or Firm* — John W. Wustenberg; Baker Botts L.L.P.

(57) ABSTRACT

Methods and apparatuses for determining surface wetting of metallic materials at downhole wellbore condition with fixed or changing well fluids are disclosed. In general, the methods according to the disclosure include carrying out an electrical impedance spectroscopy ("EIS") for a system simulating downhole conditions for the wetting of a surface by simultaneously dynamically moving electrodes exposed to the well fluid while measuring the changes in electrical characteristics between the electrodes.

10 Claims, 7 Drawing Sheets

(56) References Cited

U.S. PATENT DOCUMENTS

| | | |
|---|---|---|
| 2011/0005310 A1 | 1/2011 | Lunkad et al. |
| 2011/0061451 A1 | 3/2011 | Harris et al. |
| 2011/0198078 A1 | 8/2011 | Harrigan et al. |
| 2012/0048008 A1 | 3/2012 | Pindiprolu et al. |
| 2013/0002258 A1 | 1/2013 | Ligneul et al. |
| 2013/0013211 A1 | 1/2013 | Kumar |
| 2013/0214797 A1 | 8/2013 | Gruden |

OTHER PUBLICATIONS

International Search Report issued in PCT Application No. PCT/US2013/049648 dated Nov. 13, 2014, 4 pages.

US Statutory Invention Registration No. H1932 published Jan. 2, 2001.

International Search Report issued in PCT/US2013/049637 dated Oct. 10, 2013, 4 pages.

Silverman, D.C., "Rotating Cylinder Electrode for Velocity Sensitivity Testing", Corrosion, National Association of Corrosion Engineers, 1984, pp. 220-226.

Silverman, D.C., "The Rotating Cylinder Electrode for Examining Velocity-Sensitive Corrosion—A Review", in Critical Review of Corrosion Science and Engineering, National Association of Corrosion Engineers, 2004, pp. 1003-1023.

ASTM International, "Standard Practice for Evaluating and Qualifying Oil Field and Refinery Corrosion Inhibitors Using the Rotating Cylinder Electrode", Designation G 185-06, 8 pages.

"Electrochecmical and Corrosion Measurement in Laboratory Autoclaves" accessed at http://www.cortest.com/cormeas.htm, 4 pages.

International Preliminary Report on Patentability issued in related PCT Application No. PCT/US2013/062035, dated Apr. 7, 2016, 7 pages.

* cited by examiner

APPARATUS AND METHODS FOR DETERMINING SURFACE WETTING OF MATERIAL UNDER SUBTERRANEAN WELLBORE CONDITIONS

CROSS-REFERENCE TO RELATED APPLICATION

This application is a divisional application based on U.S. application Ser. No. 14/914,213, filed on Feb. 24, 2016, which is a national stage of and claims priority to International Patent Application Serial No. PCT/US2013/062035 filed Sep. 26, 2013, all of which are incorporated herein by reference in their entirety for all purposes.

TECHNICAL FIELD

This application is in the field of producing crude oil or natural gas from subterranean formations. More specifically, the application generally relates to methods and apparatuses for determining surface wetting under subterranean wellbore conditions.

BACKGROUND ART

To produce oil or gas, a well is drilled into a subterranean formation that is an oil or gas reservoir.

Well Servicing and Well Fluids

Generally, well services include a wide variety of operations that may be performed in oil, gas, geothermal, or water wells, such as drilling, cementing, completion, and intervention. Well services are designed to facilitate or enhance the production of desirable fluids such as oil or gas from or through a subterranean formation. A well service usually involves introducing a well fluid into a well.

Drilling is the process of drilling the wellbore. After a portion of the wellbore is drilled, sections of steel pipe, referred to as casing, which are slightly smaller in diameter than the borehole, are placed in at least the uppermost portions of the wellbore. The casing provides structural integrity to the newly drilled borehole.

Cementing is a common well operation. For example, hydraulic cement compositions can be used in cementing operations in which a string of pipe, such as casing or liner, is cemented in a wellbore. The cement stabilizes the pipe in the wellbore and prevents undesirable migration of fluids along the annulus between the wellbore and the outside of the casing or liner from one zone along the wellbore to the next. Where the wellbore penetrates into a hydrocarbon-bearing zone of a subterranean formation, the casing can later be perforated to allow fluid communication between the zone and the wellbore. The cemented casing also enables subsequent or remedial separation or isolation of one or more production zones of the wellbore, for example, by using downhole tools such as packers or plugs, or by using other techniques, such as forming sand plugs or placing cement in the perforations. Hydraulic cement compositions can also be utilized in intervention operations, such as in plugging highly permeable zones or fractures in zones that may be producing too much water, plugging cracks or holes in pipe strings, and the like.

While drilling an oil or gas well, a drilling fluid is circulated downhole through a drillpipe to a drill bit at the downhole end, out through the drill bit into the wellbore, and then back uphole to the surface through the annular path between the tubular drillpipe and the borehole. The purpose of the drilling fluid is to maintain hydrostatic pressure in the wellbore, lubricate the drill string, and carry rock cuttings out of the wellbore.

The drilling fluid can be water-based or oil-based. Oil-based fluids tend to have better lubricating properties than water-based fluids, nevertheless, other factors can mitigate in favor of using a water-based drilling fluid. Such factors may include but not limited to presence of water-swellable formations, need for a thin but a strong and impermeable filtercake, temperature stability, corrosion resistance, stuck pipe prevention, contamination resistance and production protection.

Cementing and Hydraulic Cement Compositions

Hydraulic cement is a material that when mixed with water hardens or sets over time because of a chemical reaction with the water. The cement composition sets by a hydration process, passing through a gel phase to solid phase. Because this is a chemical reaction with water, hydraulic cement is capable of setting even under water.

The hydraulic cement, water, and any other components are mixed to form a hydraulic cement composition in fluid form. The hydraulic cement composition is pumped as a fluid (typically in the form of suspension or slurry) into a desired location in the wellbore. For example, in cementing a casing or liner, the hydraulic cement composition is pumped into the annular space between the exterior surfaces of a pipe string and the borehole (that is, the wall of the wellbore). The hydraulic cement composition should be a fluid for a sufficient time before setting to allow for pumping the composition into the wellbore and for placement in a desired downhole location in the well. The cement composition is allowed time to set in the annular space, thereby forming an annular sheath of hardened, substantially impermeable cement. The hardened cement supports and positions the pipe string in the wellbore and fills the annular space between the exterior surfaces of the pipe string and the borehole of the wellbore.

Wettability and Wetting of Solid Surfaces

The wettability of a solid surface or a film on a solid surface can impact various well applications. For example, an oleaginous film on a metal surface of a tubular or a rock material of a subterranean formation can affect bonding of hydraulic cement to the surface. The wettability of rock or the wetting of the rock can affect the flow of a fluid through the matrix of rock of a subterranean formation.

Wettability involves the contact between a liquid and a solid surface, resulting from the intermolecular interactions when the two different phases are brought together. In general, the degree of wetting (wettability) depends on a force balance between adhesive forces between the liquid and solid surface and cohesive forces of the liquid (i.e., surface tensions). Adhesive forces between a liquid and solid cause a liquid drop to spread across the surface. Cohesive forces within the liquid cause the drop to ball up and avoid contact with the surface.

A measurement of the degree of wettability of a material is the contact angle, the angle at which the liquid interface meets the dry solid interface. If the wettability is very favorable to the liquid, the contact angle will be low, and the fluid will spread to cover or "wet" a larger area of the solid surface. If the wettability is unfavorable, the contact angle will be high, and the fluid will form a compact, self-contained droplet on the solid surface. If the contact angle of a water droplet on a solid surface is less than 90°, the surface may be said to be "water-wettable" (and inverse proportionally, probably not oil-wettable); whereas if the contact angle of an oil droplet on a solid surface is less than 90°, the surface may be said to be "oil-wettable" (and inverse proportionally, not water-wettable.

As used herein, a wet or wetted surface or the wetting of a surface may refer to a liquid phase that is directly in contact with and adhered to the surface of a solid body. For example, the liquid phase can be an oleaginous film on the surface of a metallic tubular or the face of a borehole in the material of a subterranean formation.

Some well fluids can form such a film or layer on a downhole surface, which can have undesirable effects. The fluid (or a liquid component of the fluid) can form a film or layer on the surface, which can act as a physical barrier between the material of the underlying solid body and a fluid adjacent to the surface of the solid body. In effect, such a film presents a different wettability characteristic than the material of the underlying solid body. For example, an oleaginous film on the surface of a metal tubular blocks water from wetting the underlying surface, which would otherwise be water-wettable.

A metallic surface of a downhole tubular is typically both water wettable and oil wettable. If first wetted with an oleaginous film, however, the oleaginous film on the metallic surface blocks the metal surface from being wettable with a water-based fluid.

Wetting of Tubulars and Formation Surfaces for Cementing

Hydraulic cement compositions do not bond well to oil-wetted surfaces. After drilling a wellbore with an oil-based drilling mud, the surfaces of tubulars and the formation in the wellbore may become oil-wetted with an oleaginous film. It is necessary to remove the film on the solid surfaces from being oil-wetted with such a film to improve cement bonding. The primary method of cleaning of oil-wet surfaces in the wellbore is through chemical and mechanical action through application of wall-shear applied at the surface due to pumping of a spacer fluid past the surface before the introduction of cement.

In a case where complete surface wetting with water is not achieved prior to placing cement in the desired zone of interest, only partial bonding of the surfaces with cement is obtained. Because of this incomplete surface bonding, there is a proportional decrease in the shear bond strength of the interface between the set cement sheath and the formation/tubular surfaces and premature interfacial de-bonding might occur under the loads experienced during the course of the well operations. This may have unwanted consequences such as interzonal communication, loss of production, and sustained casing pressure. Any of these can be detrimental to the safety and economics of hydrocarbon production from the well.

It would be highly desirable in well operations to have apparatuses and methods for determining wettability at subterranean wellbore temperature, pressure, shear, and other conditions. Applications include, for example, the designing of spacer or inverter fluids and determining the field-operational parameters for wellbore cleanout and fluid separation prior to cementing operations in a well.

SUMMARY OF THE DISCLOSURES

According to this disclosure, methods and apparatuses are provided for determining surface wetting of materials under wellbore conditions. In general, the methods disclosed herein include measuring electrical impedance spectroscopy ("EIS") for a system simulating downhole conditions for the wetting of a surface. Apparatuses are also disclosed for making EIS measurements at simulated wellbore conditions of pressure, temperature, shear and changing fluids from which the nature and quantification of the wetting of the surface for such conditions can be inferred.

These and other aspects of the disclosure will be apparent to one skilled in the art upon reading the following detailed description. While the disclosed methods and apparatuses are susceptible to various modifications and alternative forms, specific embodiments thereof will be described in detail and shown by way of example. It should be understood, however, that it is not intended to limit the disclosure to the particular forms disclosed, but, on the contrary, the intent of the disclosure is to cover all modifications and alternatives falling within the spirit and scope as expressed in the appended claims.

BRIEF DESCRIPTION OF THE DRAWING

The accompanying drawings are incorporated into the specification to help illustrate examples described herein.

FIG. 1a illustrates a drilling mud initially the annulus of the wellbore around the casing. FIG. 1b illustrates a spacer fluid being pumped through the casing to displace the drilling mud from the annulus. FIG. 1c illustrates a cement composition (sometimes referred to as a cement slurry) being pumped through the casing to displace the spacer fluid and placed in the annulus for cementing the casing in the wellbore. To seal the annulus with cement requires good cement bonding between both the outer wall of the casing and the rock of the subterranean formation of the borehole.

In FIG. 2, the spacer fluid is illustrated being pumped into the well and down through a casing (which has not yet been cemented) and then out the lower end of the casing and up through the annulus between the outside of the casing and the borehole of the wellbore. As the spacer fluid displaces the prior fluid in the wellbore, there is a diffused layer of mixing and channeling between the prior fluid and the spacer fluid. The diffused layer includes varying mixtures of the prior fluid in the well and spacer fluid. Such a diffused layer is sometimes referred to as contaminated spacer fluid. The spacer fluid being pumped behind the diffused layer is sometimes referred to as pure or uncontaminated spacer fluid.

DETAILED DESCRIPTION OF EMBODIMENTS

Figure 1:
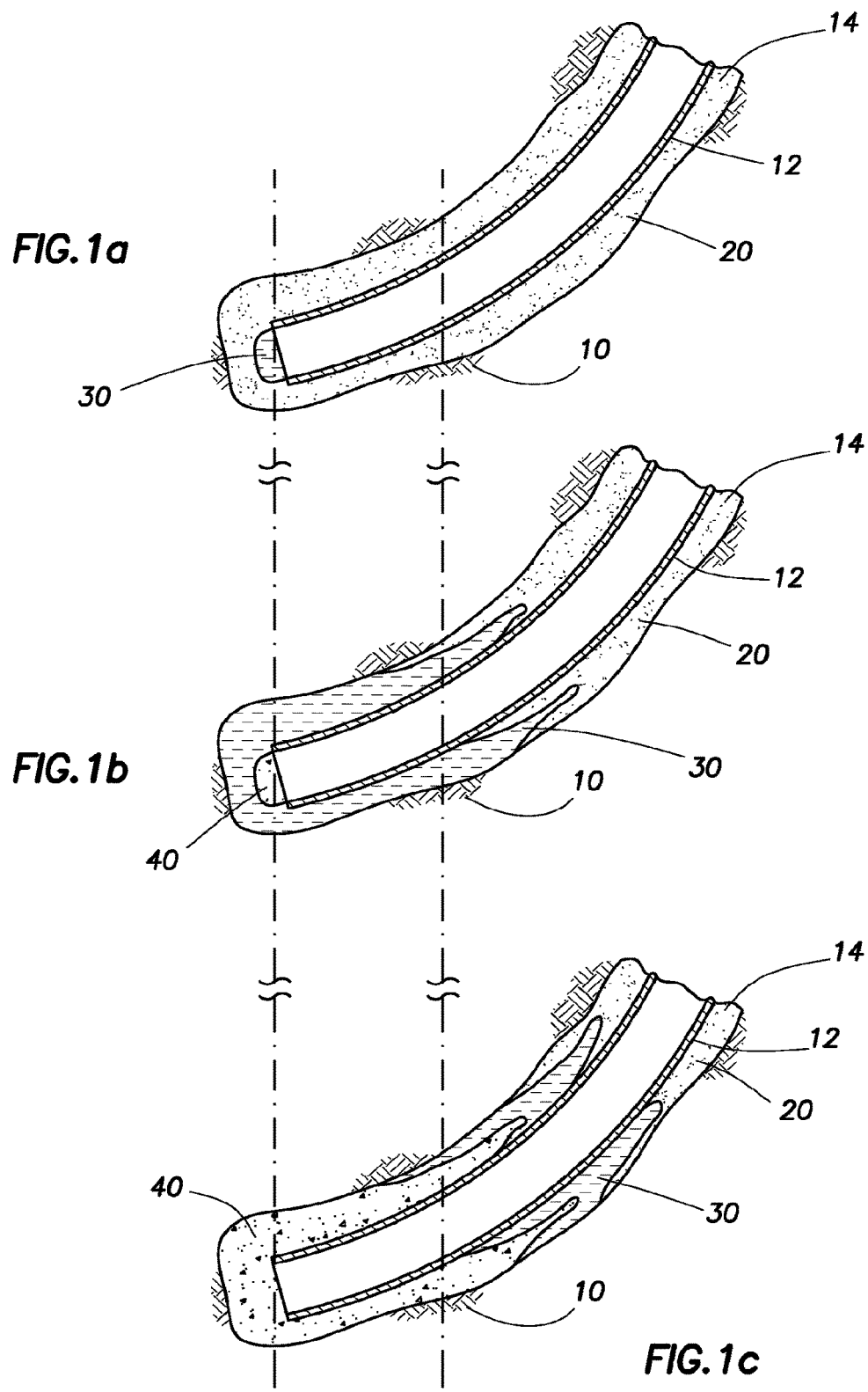
FIGS. 1a, 1b, and 1c are illustrations of a sequence of fluid displacement in a wellbore during a cementing operation. The spacer fluid is illustrated being pumped into a wellbore of a well penetrating a formation 10 and down through a casing (which has not yet been cemented) and then out the lower end of the casing and up through the annulus between the outside of the casing and the borehole of the wellbore.

Definitions and Usages
Interpretation

The words or terms used herein have their plain, ordinary meaning in the field of this disclosure, except to the extent explicitly and clearly defined in this disclosure or unless the specific context otherwise requires a different meaning.

If there is any conflict in the usages of a word or term in this disclosure and one or more patent(s) or other documents that may be incorporated by reference, the definitions that are consistent with this specification should be adopted.

The words "comprising," "containing," "including," "having," and all grammatical variations thereof are intended to have an open, non-limiting meaning. For example, a composition comprising a component does not exclude it from having additional components, an apparatus comprising a part does not exclude it from having additional parts, and a method having a step does not exclude it having additional steps. When such terms are used, the compositions, apparatuses, and methods that "consist essentially of" or "consist of" the specified components, parts, and steps are specifically included and disclosed.

The control or controlling of a condition includes any one or more of maintaining, applying, or varying of the condition. For example, controlling the temperature of a substance can include maintaining an initial temperature, heating, or cooling.

The indefinite articles "a" or "an" mean one or more than one of the component, part, or step that the article introduces.

Terms such as "first," "second," "third," etc. are assigned arbitrarily and are merely intended to differentiate between two or more components, parts, or steps that are otherwise similar or corresponding in nature, structure, function, or action. For example, the words "first" and "second" serve no other purpose and are not part of the name or description of the following name or descriptive terms. The mere use of the term "first" does not require that there be any "second" similar or corresponding component, part, or step. Similarly, the mere use of the word "second" does not require that there by any "first" or "third" similar or corresponding component, part, or step. Further, it is to be understood that the mere use of the term "first" does not require that the element or step be the very first in any sequence, but merely that it is at least one of the elements or steps. Similarly, the mere use of the terms "first" and "second" does not necessarily require any sequence. Accordingly, the mere use of such terms does not exclude intervening elements or steps between the "first" and "second" elements or steps, etc.

Well Terms

The "wellbore" refers to the drilled hole, including any cased or uncased portions of the well or any other tubulars in the well. The "borehole" usually refers to the inside wellbore wall, that is, the rock surface or wall that bounds the drilled hole. A wellbore can have portions that are vertical, horizontal, or anything in between, and it can have portions that are straight, curved, or branched. As used herein, "uphole," "downhole," and similar terms are relative to the direction of the wellhead, regardless of whether a wellbore portion is vertical or horizontal.

As used herein, the word "tubular" means any kind of body in the form of a tube. Examples of tubulars include, but are not limited to, a drill pipe, a casing, a tubing string, a line pipe, and a transportation pipe. Tubulars can also be used to transport fluids into or out of a subterranean formation, such as oil, gas, water, liquefied methane, coolants, and heated fluids. For example, a tubular can be placed underground to transport produced hydrocarbons or water from a subterranean formation to another location.

As used herein, the term "annulus" means the space between two generally cylindrical objects, one inside the other. The objects can be concentric or eccentric. Without limitation, one of the objects can be a tubular and the other object can be an enclosed conduit. The enclosed conduit can be a wellbore or borehole or it can be another tubular. The following are some non-limiting examples illustrate some situations in which an annulus can exist. Referring to an oil, gas, or water well, in an open hole well, the space between the outside of a tubing string and the borehole of the wellbore is an annulus. In a cased hole, the space between the outside of the casing the borehole is an annulus. In addition, in a cased hole there may be an annulus between the outside cylindrical portion of a tubular such as a production tubing string and the inside cylindrical portion of the casing. An annulus can be a space through which a fluid can flow or it can be filled with a material or object that blocks fluid flow, such as a packing element. Unless otherwise clear from the context, as used herein an annulus is a space through which a fluid can flow.

As used herein, a "well fluid" broadly refers to any fluid adapted to be introduced into a well for any purpose. A well fluid can be, for example, a drilling fluid, a cement composition, a treatment fluid, or a spacer fluid. If a well fluid is to be used in a relatively small volume, for example less than about 200 barrels (32 $m^3$), it is sometimes referred to as a wash, dump, slug, or pill.

Drilling fluids, also known as drilling muds or simply "muds," are typically classified according to their base fluid (that is, the continuous phase). A water-based mud ("WBM") has solid particulate (e.g., clays, bulk density increasing agents, lost circulation materials,) suspended in an aqueous liquid as the continuous phase. The water can be brine. A brine-based drilling fluid is a water-based mud in which the aqueous component is brine. In some cases, oil may be emulsified in a water-based drilling mud. An oil-based mud ("OBM") has solid particulate suspended in oil as the continuous phase. In some cases, an aqueous phase of water or brine is emulsified in the oil. Drill Cuttings from the formation will be the additional solid particulates getting suspended in both oil-based and water based muds as the drilling process begins.

As used herein, the word "treatment" refers to any treatment for changing a condition of any portion of a wellbore or an adjacent subterranean formation; however, the word "treatment" does not necessarily imply any particular treatment purpose. A treatment usually involves introducing a well fluid for the treatment, in which case it may be referred to as a treatment fluid, into a well. As used herein, a "treatment fluid" is a fluid used in a treatment. The word "treatment" in the term "treatment fluid" does not necessarily imply any particular treatment or action by the fluid.

As used herein, the terms spacer fluid, wash fluid, and inverter fluid can be used interchangeably. A spacer fluid is a fluid used to physically separate one special-purpose fluid from another. It may be undesirable for one special-purpose fluid to mix with another used in the well, so a spacer fluid compatible with each is used between the two. A spacer fluid is usually used when changing between well fluids used in a well.

For example, a spacer fluid is used to change from a drilling fluid during drilling to cement composition during cementing operations in the well. In case of an oil-based drilling fluid, it should be kept separate from a water-based cementing fluid. In changing to the latter fluid, a chemically treated water-based spacer fluid is usually used to separate the drilling fluid from the water-based cementing fluid.

A spacer fluid specially designed to separate a special purpose oil-external fluid from a special purpose water-external fluid may be termed as an inverter fluid. Inverter fluids may be so designed that the diffused contaminated layer between both the special purpose fluids has progressive variation in properties like solids carrying capability, electrical conductivity, rheology, and chemical potential. In other words, inverter fluids may be ideally designed to be fully compatible physically and chemically with either or both of the special purpose fluids under the simulated conditions of pressure, temperature and shear. Compatibility may be warranted by rheological investigations or visual observations at all intermediate compositions. Unwanted flocculation, coagulation, or excessive thinning of the admixture compared to the original fluids is typically considered to be a signature for incompatibility.

As used herein, a downhole fluid is an in-situ fluid in a well, which may be the same as a well fluid at the time it is introduced, or a well fluid mixed with another fluid downhole, or a fluid in which chemical reactions are occurring or have occurred in-situ downhole.

Generally, the greater the depth of the formation, the higher the static temperature and pressure of the formation. Initially, the static pressure equals the initial pressure in the formation before production. After production begins, the static pressure approaches the average reservoir pressure.

A "design" refers to the estimate or measure of one or more parameters planned or expected for a particular stage of a well service or associated well fluid. For example, a fluid can be designed to have components that provide a minimum viscosity for at least a specified time under expected downhole conditions. A well service may include design parameters such as fluid volume to be pumped, required pumping time for a treatment, or the shear conditions of the pumping, and contact time of a treatment fluid with a zone of interest.

The term "design temperature" refers to an estimate or measurement of the actual temperature at the downhole environment at the time of a well treatment. That is, design temperature takes into account not only the bottom hole static temperature ("BHST"), but also the effect of the temperature of the well fluid on the BHST during treatment. The design temperature is sometimes referred to as the bottom hole circulation temperature ("BHCT"). Because treatment fluids may be considerably cooler than BHST, the difference between the two temperatures can be quite large. Ultimately, if left undisturbed, a subterranean formation will return to the BHST.

Fluids

A fluid can be a single phase or a dispersion. In general, a fluid is an amorphous substance that is or has a continuous phase of particles that are smaller than about 1 micrometer that tends to flow and to conform to the outline of its container.

Examples of fluids are gases and liquids. A gas (in the sense of a physical state) refers to an amorphous substance that has a high tendency to disperse (at the molecular level) and a relatively high compressibility. A liquid refers to an amorphous substance that has little tendency to disperse (at the molecular level) and relatively high incompressibility. The tendency to disperse is related to Intermolecular Forces (also known as van der Waal's Forces). (A continuous mass of a particulate, e.g., a powder or sand, can tend to flow as a fluid depending on many factors such as particle size distribution, particle shape distribution, the proportion and nature of any wetting liquid or other surface coating on the particles, and many other variables. Nevertheless, as used herein, a fluid does not refer to a continuous mass of particulate because the sizes of the solid particles of a mass of a particulate are too large to be appreciably affected by the range of Intermolecular Forces.)

As used herein, a fluid is a substance that behaves as a fluid under Standard Laboratory Conditions, that is, at 77° F. (25° C.) temperature and 1 atmosphere pressure, and at the higher temperatures and pressures usually occurring in subterranean formations without applied shear.

Every fluid inherently has at least a continuous phase. fluid can have more than one phase. The continuous phase of a well fluid is a liquid under Standard Laboratory Conditions. or example, a well fluid can in the form of be a suspension (solid particles dispersed in a liquid phase), an emulsion (liquid particles dispersed in another liquid phase), or a foam (a gas phase dispersed in liquid phase).

As used herein, a water-based fluid means that water or an aqueous solution is the dominant material of the continuous phase, that is, greater than 50% by weight, of the continuous phase of the substance.

In contrast, "oil-based" means that oil is the dominant material by weight of the continuous phase of the substance. In this context, the oil of an oil-based fluid can be any oil. In general, an oil is any substance that is liquid Standard Laboratory Conditions, is hydrophobic, and soluble in organic solvents. Oils have a high carbon and hydrogen content and are relatively non-polar substances, for example, having a dielectric constant of 1.5 to 5. This general definition includes classes such as petrochemical oils, vegetable oils, and many organic solvents. All oils can be traced back to organic sources.

Apparent Viscosity of a Fluid

Viscosity is a measure of the resistance of a fluid to flow. In everyday terms, viscosity is "thickness" or "internal friction." Thus, pure water is "thin," having a relatively low viscosity whereas honey is "thick," having a relatively higher viscosity. Put simply, the less viscous the fluid is, the greater its ease of movement (fluidity). More precisely, viscosity is defined as the ratio of shear stress to shear rate.

A fluid moving along solid boundary will incur a shear stress on that boundary. The no-slip condition dictates that the speed of the fluid at the boundary (relative to the boundary) is zero, but at some distance from the boundary, the flow speed must equal that of the fluid. The region between these two points is named the boundary layer.

A Newtonian fluid (named after Isaac Newton) is a fluid for which stress versus strain rate curve is linear and passes through the origin. The constant of proportionality is known as the viscosity. Examples of Newtonian fluids include water and most gases. Newton's law of viscosity is an approximation that holds for some substances but not others.

Non-Newtonian fluids exhibit a more complicated relationship between shear stress and velocity gradient (i.e., shear rate) than simple linearity. Thus, there exist a number of forms of non-Newtonian fluids. Shear thickening fluids have an apparent viscosity that increases with increasing the rate of shear. Shear thinning fluids have a viscosity that decreases with increasing rate of shear. Thixotropic fluids become less viscous over time at a constant shear rate. Rheopectic fluids become more viscous over time at a constant sear rate. A Bingham plastic is a material that behaves as a solid at low stresses but flows as a viscous fluid at high stresses.

Most well fluids are non-Newtonian fluids. Accordingly, the apparent viscosity of a fluid applies only under a particular set of conditions including shear stress versus shear rate, which must be specified or understood from the context. As used herein, a reference to viscosity is actually a reference to an apparent viscosity. Apparent viscosity is commonly expressed in units of centipoise ("cP").

Like other physical properties, the viscosity of a Newtonian fluid or the apparent viscosity of a non-Newtonian fluid may be highly dependent on the physical conditions, primarily temperature and pressure.

Viscosity Measurements

There are numerous ways of measuring and modeling viscous properties, and new developments continue to be made. The methods depend on the type of fluid for which viscosity is being measured. A typical method for quality assurance or quality control (QA/QC) purposes uses a Couette device, such as a Fann Model 35 or 50 viscometer or a Chandler 5550 HPHT viscometer, that measures viscosity as a function of time, temperature, and shear rate. The viscosity-measuring instrument can be calibrated, for example, by using standard viscosity silicone oils or other standard viscosity fluids.

Unless otherwise specified, the apparent viscosity of a fluid (excluding any suspended solid particulate larger than silt) is measured with a Fann Model 35 type viscometer using an R1 rotor, B1 bob, and F1 torsion spring at a shear rate of 40 l/s, and at a temperature of 77° F. (25° C.) and a pressure of 1 atmosphere. For reference, the viscosity of pure water is about 1 cP.

A substance is considered to be a fluid if it has an apparent viscosity less than 5,000 cP (independent of any gel characteristic).

Cement Compositions

As used herein, "cement" refers to an inorganic cement (as opposed to organic cement and adhesives) that when mixed with water will begin to set and harden.

As used herein, a "cement composition" is a material including at least cement. A cement composition can also include additives. A cement composition can include water or be mixed with water.

A cement can be characterized as non-hydraulic or hydraulic.

Non-hydraulic cements (e.g., gypsum plaster, Sorel cements) must be kept dry in order to retain their strength.

Hydraulic cements (e.g., Portland cement) harden because of hydration, chemical reactions that occur independently of the mixture's water content; they can harden even underwater or when constantly exposed to wet weather. The chemical reaction that results when the dry cement powder is mixed with water produces hydrates that have extremely low solubility in water The cement composition sets by a hydration process, and it passes through a gel phase to solid phase.

During well completion, it is common to introduce a cement composition into an annulus in the wellbore. For example, in a cased hole, the cement composition is placed into and allowed to set in the annulus between the wellbore and the casing in order to stabilize and secure the casing in the wellbore. After setting, the set cement composition should have a low permeability. Consequently, oil or gas can be produced in a controlled manner by directing the flow of oil or gas through the casing and into the wellhead. Cement compositions can also be used, for example, in well-plugging operations or gravel-packing operations.

Surfactant or Emulsifier

As used herein, a surfactant or emulsifier refers to a substance that helps prevent the droplets of the dispersed phase of an emulsion from flocculating or coalescing in the emulsion. The efficacy of a surfactant is known to be measured using techniques like penetrative displacement and immersion wetting and using parameters like spreading coefficient and partition coefficient.

Surfactants contain both hydrophobic and hydrophilic groups, that is, a molecule that contains both oil soluble as well as water-soluble components. These molecules diffuse in water and adsorb at interfaces between oil and water. The insoluble hydrophobic group extends out from the water phase towards the oil phase while the water-soluble group remains in the water phase. Alignment of these molecules modifies the surface properties of the oil-water interface.

A surfactant or emulsifier can be or include a cationic, a zwitterionic, or a nonionic emulsifier. A surfactant package can include one or more different chemical surfactants.

A surfactant package may be included in a fluid that is being deployed for a clean-out operation. The surfactant package may include one or more water-soluble surfactants, one or more oil soluble surfactants, and one or more emulsifiers.

A Method According to the Present Disclosure

According to an embodiment, a method is provided including the steps of:

(A) obtaining or providing an apparatus comprising:
(i) a container forming a chamber;
(ii) a first surface exposed to or in the chamber, wherein the first surface is a first electrode,
(iii) a second surface exposed to or in the chamber, wherein the second surface is a second electrode,
wherein the first surface is electrically insulated from the second surface;

(B) wetting at least the first surface with a first fluid in liquid phase;

(C) after the step of wetting, introducing a second fluid in liquid phase into the chamber, wherein the second liquid is immiscible with the first liquid phase;

(D) moving the first and second surfaces while immersed in the fluid in the chamber to apply shear between the fluid in the chamber and the first and second surfaces; and (E) making an electrical impedance spectroscopy measurement between the first and second electrode.

According to another embodiment of this method, it additionally includes the steps of: before the step of applying the shear, making a first electrical impedance spectroscopy measurement between the first and second electrode; during or after the step of applying the shear, making a second electrical impedance spectroscopy measurement between the first and second electrode; comparing the first electrical impedance spectroscopy measurement to the second electrical impedance spectroscopy measurement; and based on the step of comparing, inferring any changes in the wetting of the first surface. Preferably, the step of inferring comprises assuming an equivalent electrical circuit model to match experimental impedance changes using non-linear regression techniques.

According to a further embodiment, the method additionally includes making an electrical impedance spectroscopy measurement after the introduction of a second fluid.

According to yet another embodiment of this method, it additionally includes the step of maintaining the electrodes at the subterranean wellbore conditions of pressure, temperature while applying shear and while making an electrical impedance spectroscopy measurement between the first and second electrode.

According to a further embodiment, the step of taking an electrical impedance spectroscopy measurement includes: operatively connecting an alternating electrical potential source between the first and second electrodes; while operatively connected to the first and second electrodes, varying the electrical potential or the frequency of the alternating electrical potential source; and while varying the electrical potential or the frequency of the alternating electrical potential source, measuring electrical impedance between the first electrode and second electrode to obtain an electrical impedance spectroscopy measurement.

An Apparatus According to the Present Disclosure

According to an embodiment, an apparatus is provided comprising:
 (A) a container forming a chamber containing a fluid;
 (B) first and second surfaces in the chamber contacting the fluid;
 (C) means for moving the first and second surfaces in the chamber; and
 (D) means connected to the first and second surfaces for measuring electrical impedance between the first and second surfaces whereby electrical impedance spectroscopy measurements can be made between the first surface and second surface.

According to another embodiment, an apparatus is provided including:
 (A) a container forming a chamber;
 (B) a fluid in the chamber;
 (C) a first surface in the chamber in contact with the fluid, wherein the first surface is a first electrode;
 (D) a second surface in the chamber in contact with the fluid, wherein the second surface is a second electrode, and wherein the first surface is electrically insulated from the second surface;
 (E) a shear assembly connected to the first and second surfaces for simultaneously moving the first and second surfaces in the chamber;
 (F) a means for controlling the shear rate of shear assembly by controlling the movement of the first and second surfaces;
 (G) an alternating electrical potential source operatively connected between the first and second electrodes;
 (H) means for controlling the electrical potential or the frequency of the alternating electrical potential source; and
 (I) means for measuring changes in electrical impedance between the first electrode and second electrode;

whereby electrical impedance spectroscopy measurements can be made between the first electrode and the second electrode before, during, or after controlling the shear rate.

According to an additional embodiment of this apparatus, it includes means for maintaining the electrodes at the subterranean wellbore conditions of pressure and temperature while making an electrical impedance spectroscopy measurement between the first and second electrode before, during, or after controlling the shear rate.

According to another embodiment of this apparatus, the first surface and second surfaces are mounted on a bob that rotates in fluid in a chamber.

According to further embodiment of this apparatus, the first surface and second surfaces are mounted circumferentially spaced on a bob that rotates in the fluid in the chamber.

According to an even further embodiment of this apparatus, means are provided to measure viscosity of the fluid in the chamber while moving the surfaces in the fluid in the chamber.

Applications of the Disclosure

Various fluids and surfactants are used in wells that may change the wettability or wetting of downhole solid surfaces.

This disclosure relates to techniques that can be used to test, under simulated downhole conditions, the surface wetting, film cleaning capability, or other effect of a fluid on various surfaces. The test can be used, for example, to test and quantify the water-wetting efficiency of a fluid that is to be pumped into a well. The test can be used to test, under simulated conditions, the wetted status of a downhole surface after exposure to a downhole fluid.

According to an embodiment of the disclosure, a technique of electrical impedance spectroscopy can be used to measure the percentage area of coverage by water or, conversely, area of coverage by oil on a surface under conditions that simulate downhole conditions in a well. The percentage of surface wetting with water or oil can be measured using this method, non-invasively and without the use of visual inspection, or imaging, or goniometry methods that have been known to be associated with error and non-repeatability.

In an embodiment, the disclosure can be useful in determining the wettability or wetting of surfaces in wells, including the surfaces of a tubular and/or a subterranean formation. This information is used in the design of various well services and well fluids.

An embodiment can be used for designing well fluids such as drilling fluids, spacer fluids, and cement compositions, or for designing the conditions of introducing such well fluids into a well.

Applications to Cementing

Hydraulic cement does not bond to oil-wet surfaces. Surface wettability with water is of primary importance to achieve good cement bonding to a metallic pipe. It is also important to achieve good cement bonding to adjacent rock surfaces of a subterranean formation. The quality of a cement bond to a surface can be expected to be best if 100% water wetting of the surface is achieved.

The cement-steel interface is weaker than the bulk of the cement itself. Increased chances of loss of zonal isolation occur if the complete surface area is not bonded to the cement. Any reduction in the percentage of water-wet area increases the non-bonded area, thereby reducing the shear bond strength of the cement sheath and its competence to isolate zones.

A water-wetted metal surface allows for the formation of a stronger and more completely bonded cement-steel interface. Similarly, a water-wetted rock surface of a subterranean formation allows for the formation of a stronger and more completely bonded cement-rock interface. Accordingly, in a cementing operation, it is important to try to change an oil-wetted surface to a water-wetted surface prior to placing the cement composition in the portion of the wellbore to be cemented.

FIGS. 1a, 1b, and 1c are illustrations of a sequence of fluid displacement in a wellbore during a cementing operation. A spacer fluid 30 is illustrated being pumped into a wellbore of a well penetrating a formation 10 and down through a casing 12 (which has not yet been cemented) and then out the lower end of the casing and up through the annulus 14 between the outside of the casing 12 and the borehole of the wellbore. FIG. 1a illustrates a drilling mud 20 initially in the annulus 14 of the wellbore around the casing 12. FIG. 1b illustrates a spacer fluid 30 being pumped through the casing to displace the drilling mud 20 from the annulus 14. FIG. 1c illustrates a cement composition 40 (sometimes referred to as a cement slurry) being pumped through the casing 12 to displace the spacer fluid 30 and placed in the annulus 14 for cementing the casing 12 in the wellbore penetrating the formation 10. To seal the annulus 14 with cement requires good cement bonding between both the outer wall of the casing 12 and the rock of the subterranean formation 10 of the borehole.

Figure 2:
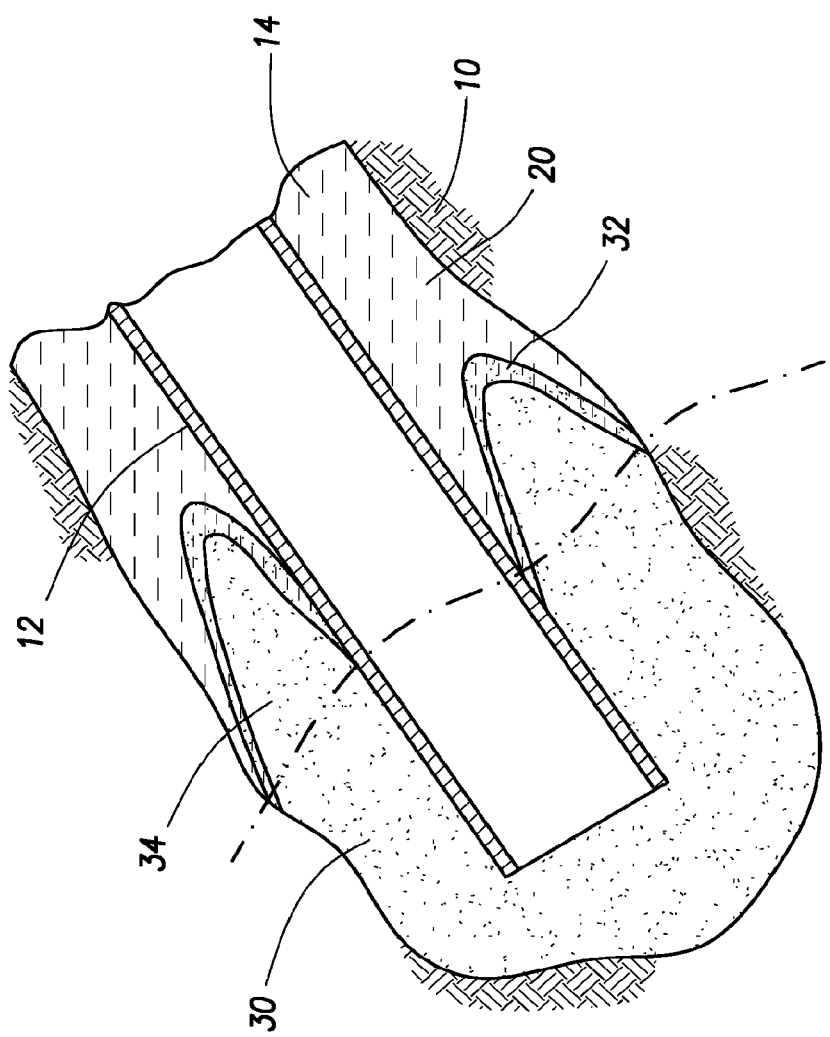
FIG. 2 is an illustration modeling fluid intermixing between a prior drilling mud in a wellbore and a spacer fluid as the spacer fluid displaces the prior well fluid, which is similar to the stage illustrated in FIG. 1b.

FIG. 2 is an illustration modeling of fluid intermixing between a prior well fluid, such as a drilling mud 20, in a wellbore penetrating a subterranean formation 10 and a spacer fluid 30 as the spacer fluid displaces the prior drilling mud 20, which is similar to the stage illustrated in FIG. 1b. In FIG. 2, the spacer fluid 30 is illustrated being pumped into the well and down through a casing 12 (which has not yet been cemented) and then out the lower end of the casing and up through the annulus 14 between the outside of the casing and the borehole of the wellbore penetrating the subterranean formation 10. As the spacer fluid displaces the prior fluid in the wellbore, there is a diffused layer 32 of mixing and channeling between the prior fluid and the spacer fluid. The diffused layer 32 includes varying mixtures of the prior fluid in the well and spacer fluid. The diffused layer 32 is sometimes referred to as contaminated spacer fluid. The spacer fluid 30 being pumped behind the diffused layer is sometimes referred to as pure or uncontaminated spacer fluid.

A method according to this disclosure can be used to test the effectiveness of a water-based spacer fluid for removing an oil-based drilling fluid and rendering downhole surfaces water wet prior to cement slurry placement. This method can be used to optimize the dosage of costly surfactant packages, annular pump rates, and contact times in spacer fluids at downhole conditions. In addition, the method can be extended to perform quality check on cement to pipe bonding after cement setting.

Fundamental Electrical Concepts

A conductor is a substance that contains movable electric charges. In metallic conductors such as copper or aluminum, the movable charged particles are electrons (see electrical conduction). Positive charges may also be mobile, such as the cationic electrolyte(s) of a battery, or the mobile protons of the proton conductor of a fuel cell. In general, the term wire refers to an elongated conductor.

An insulator is a non-conducting substance with few mobile charges and which support only insignificant electric currents.

The electrical resistance of an electrical element is the opposition to the passage of an electric current through that element; the inverse quantity is electrical conductance, the ease at which an electric current passes. The SI unit of electrical resistance is the ohm (a), while electrical conductance is measured in siemens (S).

Electrical Impedance Spectroscopy to Test Wetting in a Complex System

Well fluids and downhole surface conditions are complex systems. In dealing with particle-laden well fluids on irregular and rough surfaces, the concept of ideal capacitor may turn out to be insufficient. Temperature, ionic concentration, types of ions, oxide layers, adsorptive species, and surface roughness influence electrical double layer capacitance. According to this disclosure, these are modeled as capacitors that are leaky and that have non-uniform current distribution. In addition, when a surface is polarized, it can cause current to flow through electrical interactions that are induced to occur at or near the surface. These effects can be modeled using parameters known as polarization resistance and charge transfer resistance. Electrical interactions accompanied by mass transfer are modeled using a parameter known as Warburg Impedance.

According to the present disclosure, a combination of resistors and capacitors is used to model the impedance offered by a system. The impedance offered by the system is physically measured and subsequent mathematical modeling is carried out to calculate the values of the resistances and capacitances of the individual electrical elements. These values will be an indication of the completeness of water wetting on the surface.

An electrical circuit is completed in order to measure the impedance of the system. This can be done by building an electrical system with an oil-field well fluid.

In general, an AC circuit is used to measure impedance at a perturbation voltage and various frequencies.

Electrical properties that influence charge conductance or accumulation associated with the surfaces can be additionally modeled with this technique to study or simulate changes in the wetting on a surface in a well.

Figure 3A:
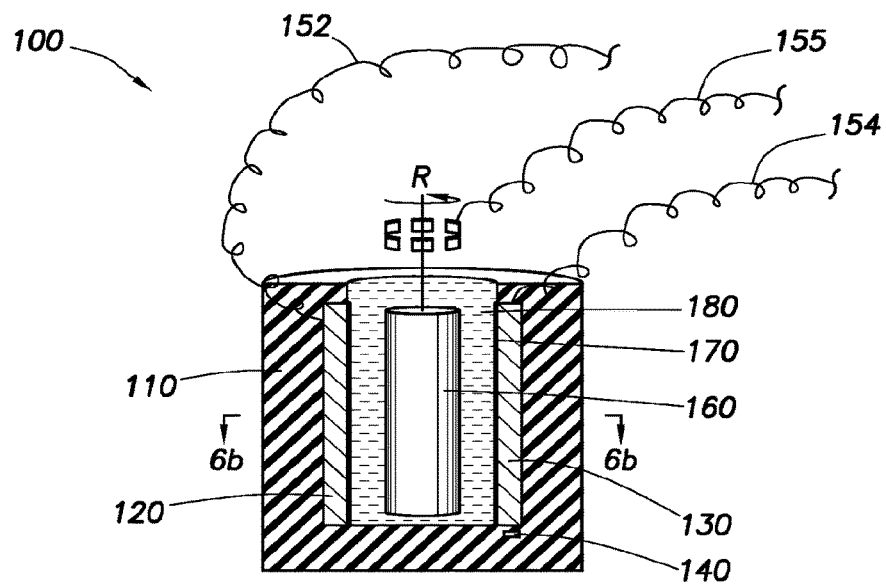
FIG. 3a is a vertical cross-sectional view of an apparatus for measuring the change in surface wetting on a metal surface, which can be selected, for example, to simulate a metal surface in a well. The electrical circuit for measuring electrical impedance between the electrodes of the apparatus is not shown in detail.
Figure 3B:
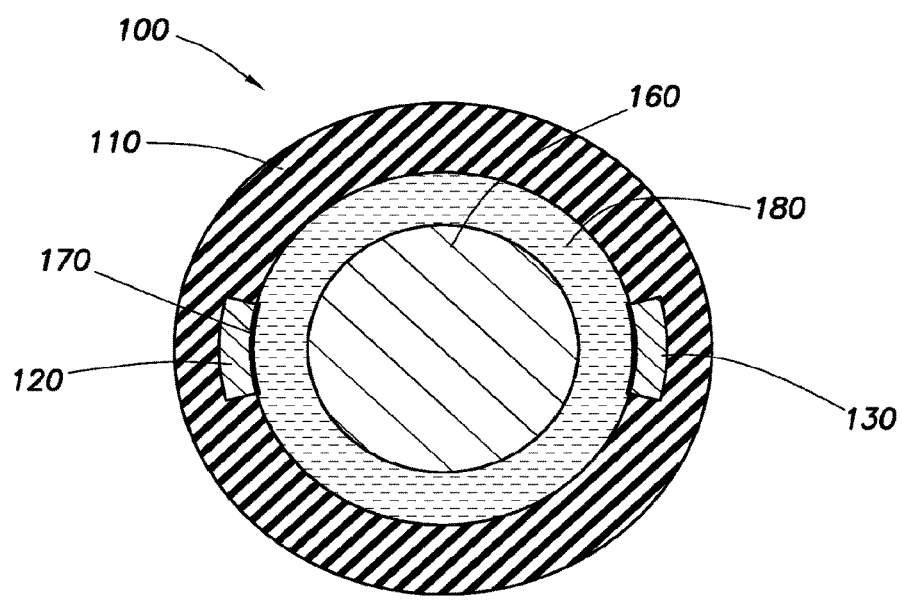
FIG. 3b is a top view of the apparatus in FIG. 3a, illustrating the insulated separation of the electrodes in the container wall of the apparatus. This type of apparatus can measure the change in surface wetting on an electrode surface from a first liquid phase to a second liquid phase as a second fluid including the second liquid phase is sheared in the container of the apparatus at a controlled rate for a controlled contact time. The electrode surfaces can simulate the metallic body of a tubular. The first liquid phase can simulate a prior oleaginous film formed on the surface. The second fluid can and conditions of shear and time can simulate the displacement of the oleaginous film by a spacer fluid.

According to an embodiment for simulating downhole conditions on a metallic surface, an electrical system 100 is schematically represented, in FIG. 3a and FIG. 3b. As shown in FIG. 3a, the electrical system 100 includes: an electrically insulating electrode holder or container 115, a first electrode 120; a second electrode 130, an optional reference electrode 140, a motor (not shown) for providing rotational speed R to a structure 160 for shearing a fluid in the container 115, wires 152 and 154 operatively connected between the first electrode 120 and the second electrode 130, respectively, to an EIS measuring device (not shown in this figure). Alternatively, wire 155 is connected to the shaft of the rotating structure 160 through brushes. In this embodiment the structure 160 comprises and electrode and the EIS measurements are made between wire 155 and either or both wires 152 and 154.

The primary method of cleaning of oil wet surfaces in the well bore is through chemical and mechanical action through application of wall-shear applied at the surface due to flow of the spacer. In order to mimic the pumping process in the wellbore, in laboratory test cell, structure 160 is provided to apply a wall-shear rate through rotation. The rotation of the structure 160 immersed in the fluid generates the shear in the fluid and thus simulates the cleaning. For rotation, the structure 160 is provided with a drive mechanism (not shown) which can be a stepper motor or any other motor which is positively engaged to the bob or it can be a "Mag Drive" which uses the wireless coupling of magnetic fields as a means of torque transmission. Various geometrical configurations for the structure 160 have been used by rheologists to create shear and characterize the flow behavior of fluids. The more common ones are bob/sleeve (couette) and impeller (mixer) geometries. Although, the structure 160 is illustrated as a bob/sleeve form suspended form a rotating shaft, it is anticipated that impellers and other impellers and shapes could be used.

This system 100 is adapted for simulating and measuring the formation or removal of any wetting or coating or film 170 on the surfaces the electrodes 120 or 130 in the presence of a test fluid 180. The changes can be measured under shearing conditions applied to the test fluid 180 in the system 100. The composition of the test fluid 180 can be kept constant during a testing procedure or it can be changed continuously or intermittently by dosing another test fluid that displaces the original fluid under controlled hydrodynamic conditions. In general, the system and applied voltage is adapted such that the electrical circuit is directed across the electrodes 120 and 130 through the test fluid 180. FIG. 3b is a top view of FIG. 3a.

One or both the electrodes 120 and 130 can be used to simulate a downhole metallic or formation material, such as, a steal tubular and formation rock. The test conditions of shear, and optionally temperature and pressure can be adapted to simulate downhole conditions adjacent a downhole at a subterranean location, and the test fluid can be used to simulate a well fluid in a wellbore. In general, the system 100 can be used, as described herein, to measure any changes in any surface wetting or film 170 on the test electrodes under such simulated test conditions and with such test fluids.

The system 100 can be used to determine the removal of a film or coating on an metallic electrode surface that is needed to be removed under the effect of shear, pressure, temperature, and time conditions as may be used in the wellbore. Here, the coating can be deliberately created by applying a coating manually or can be automatically created during the process of shearing the fluid which is responsible for applying the coating in the setup. In this case, the contents and ingredients of the coating will be present in the first fluid. The second fluid will be used to remove the coating.

For example, electrodes made of casing grade material are used. The electrodes are first made oil wet using the oil based drilling fluid and are then dipped in a spacer bath. Shear is then applied to the spacer to simulate pumping and the impedance between the electrodes is successively measured to check for the degree of oil wetness. In another example the electrodes are firs made water wet by a water based drilling fluid and are then dipped in a spacer bath, shear applied and impedance measured.

Figure 4:
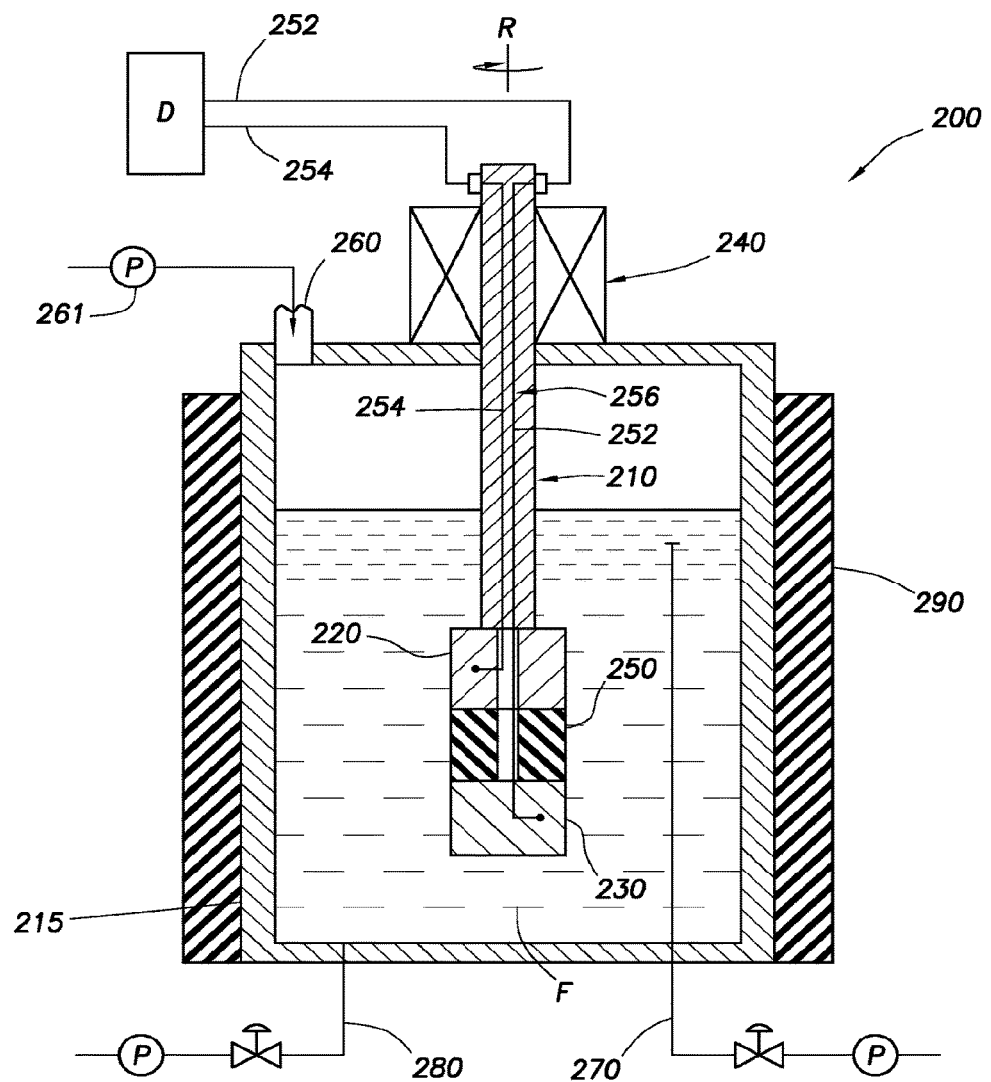
FIG. 4 is a vertical cross-sectional view of an apparatus for measuring the change in surface wetting on a metal surface, which can be selected, for example, to simulate a metal surface in a well.

According to a further embodiment for simulating downhole conditions on a metallic surface, an electrical system 200 is schematically represented, in FIG. 4. In this embodiment, the electrodes are mounted on the bob which creates and adequate fluid-shear rate. As shown in FIG. 4, the electrical system 200 includes: a bob assembly 210 comprising an electrically insulated electrode holder, a first electrode 220; a second electrode 230, and a drive unit 240 for providing rotational speed R to the bob assembly 210 for shearing a fluid F in the container 215. Wires 252 and 254 are operatively connected to the first electrode 220 and the second electrode 230, respectively, and to an EIS measuring device D. In this embodiment, the drive unit 240 is an electrical powered motor which can be either a conventional motor or stepper motor which is operably connected to rotate the bob and move the surfaces in the test fluid.

In this embodiment, the bob 210 has a hollow shaft 256 with insulated wires 252 and 254 passing through the center of the shaft 256. As in the previous and following embodiments the shear creating structure is illustrated in the bob/sleeve form suspended form a rotating shaft, however, any other geometry capable of creating a measurable, repeatable shear application on the electrodes can be used. Bearing and rotary seals (not shown) provided in the wall of the container 215 mount the shaft 256 to rotate at speed R and provide a fluid seal around the shaft 256 where the shaft passes through the container wall. Slip rings and brushes (not shown) can be provided on the shaft to connect the stationary EIS measuring device D to the wires 252 and 254. In another embodiment, the shaft is conductive material and acts as a conductor for one of the electrodes. In a further embodiment, concentric telescoped insulated shafts are provided as conductors for the electrodes.

Each of the first and second electrodes 220 and 230 comprise cylindrical shaped sections mounted on the shaft 256 and along with the cylindrical shape insulator 250 form the bob 210. The cylindrical shape insulator 250, mounted on the shaft separates and isolates the first electrode 220 from the second electrode 230. If the shaft 256 comprised conductive materials, such as a metal, the electrodes 220 and 230 are mounted such that they are electrically insulated from the shaft.

The container 215 in this system comprises a sealed pressure vessel capable of withstanding internal pressures and temperatures. Containers capable of functioning in the high pressure—high temperature range of those present in subterranean wells. Container 215 includes a pressurization port 260 connected to a pump 261 for pressurizing the fluid in the interior of the container. The test fluid F can be tested in the container 215 at pressures ranging for example, from atmospheric to 12,000 psi. Container 215 can also have at least one additional port 270 for adding and/or removing test fluids when the pressurization port is not used for that purpose. Additional ports 280 can also be present in the container at different horizontal levels in the container 215. These ports can be connected to valves, pressure regulators, pumps and the like as required to insert and remove fluid from the container. By using the ports 270 and 280 test fluid F can be changed continuously or intermittently during wettability testing by adding another test fluid that displaces the original fluid under controlled hydrodynamic conditions.

A heater and insulating jacket 290 can also be provided around the container 215 to perform wettability testing at elevated temperatures simulating subterranean wellbore conditions. In this manner testing can be performed with the test fluid F at elevated temperatures from atmospheric to as high as 350° F. Suitable temperature and pressure sensors can be provided in the container (not shown) to monitor the temperature and pressure of the test fluid.

This system 200 is adapted for simulating and measuring the formation and/or removal of any wetting or coating or film on the surfaces the electrodes 220 or 230 in the presence of a first test fluid. The changes can be measured under shearing conditions applied to the first test fluid in the system 200 which replicate those present in the well. The composition of the test fluid can be kept constant during a testing procedure or it can be changed continuously or intermittently by dosing another test fluid that displaces the original fluid under controlled hydrodynamic conditions. In general, the system and applied voltage is adapted such that the electrical circuit is directed across the electrodes 220 and 230 through the test fluid.

One or both the electrodes 220 and 230 can be used to simulate a downhole metallic or formation material, such as a steal tubular or formation rock, the test conditions of shear, and optionally temperature and pressure can be adapted to simulate downhole conditions adjacent a downhole material, and the test fluid can be used to simulate a well fluid in a wellbore. In general, the system 200 can be used, as described herein, to measure any changes in any surface wetting or film on the test electrodes under such simulated test conditions and with such test fluids.

Figure 5:
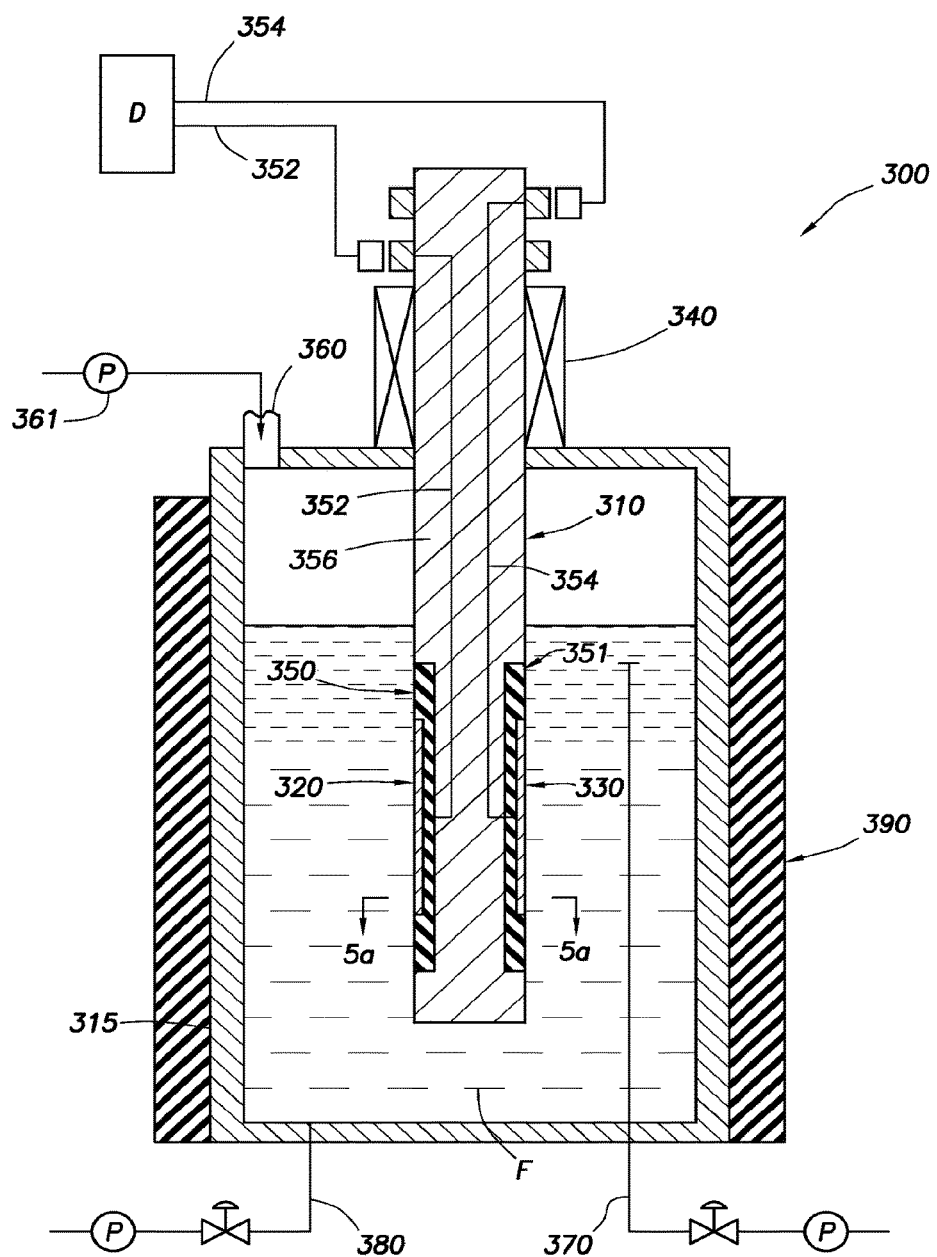
FIG. 5 is a vertical cross-sectional view of an apparatus for measuring the change in surface wetting on a metal surface, which can be selected, for example, to simulate a metal surface in a well.
Figure 5A:
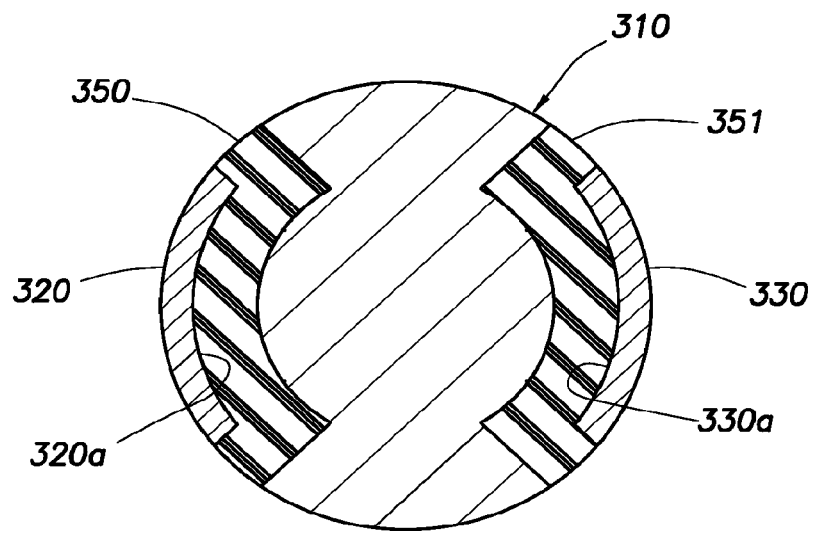
FIG. 5a is a horizontal section illustrating the shape and placement of the electrodes in a bob.

According to an additional embodiment for simulating downhole conditions on a metallic surface, an electrical system 300 is schematically represented, in FIGS. 5 and 5a. In FIGS. 5 and 5a the corresponding parts and components of the system 200 are referred to in system 300 using reference numbers with the most significant digit being a 3 instead of a 2. In FIGS. 5 and 5a, the electrical system 300 is identical to the embodiment illustrated in FIG. 4, except that the bob assembly 310 is structured differently from the bob assembly 210.

In this embodiment the rotating bob 310 comprises an electrically insulated electrode holder, a first electrode 320; a second electrode 330, and insulators 350 and 351. Bob assembly 310 has a solid cylindrical shaft 356 and wires 352 and 354 formed or embedded in the shaft 356. Wires 352 and 354 are operatively connected to the first electrode 320 and the second electrode 330, respectively and to an EIS measuring device D The insulators 350 and 351 each have cylindrical segment shaped outer walls and each is mounted on the shaft 356 to rotate with the bob 310. Each of the first and second electrodes 320 and 330 comprise also segments of a cylindrical wall mounted in pockets or recesses 320a and 330a in the outer surface of the insulator 350. Insulators 350 and 351 isolate the first electrode 320 from the second electrode 330. If the shaft 356 comprised conductive materials such, as a metal, the electrodes 320 and 330 are mounted such that they are electrically insulated from the shaft.

One or both the electrodes 320 and 330 can be used to simulate a downhole metallic or formation material, such as a steal tubular or formation rock, the test conditions of shear, and optionally temperature and pressure can be adapted to simulate downhole conditions adjacent a downhole material, and the test fluid can be used to simulate a well fluid in a wellbore. In general, the system 300 can be used, as described herein, to measure any changes in any surface wetting or film on the test electrodes under such simulated test conditions and with such test fluids. As the bob is rotated, the electrodes move in the test fluid to replicate shear at that is present in the actual wellbore, while the test fluid is at formation temperature and pressure while measuring electrical impedance spectroscopy.

The system 300 can be used to determine the removal of a film or coating on an metallic electrode surface that is needed to be removed under the effect of shear, pressure, temperature, and time conditions as may be used in the wellbore. Here, the coating can be deliberately created by applying a coating manually or can be automatically created during the process of shearing the fluid which is responsible for applying the coating in the setup. In this case, the contents and ingredients of the coating will be present in a first fluid. The second fluid will be used to remove the coating.

This system 300 is adapted for performing the methods described with respect to FIG. 4.

Figure 6:
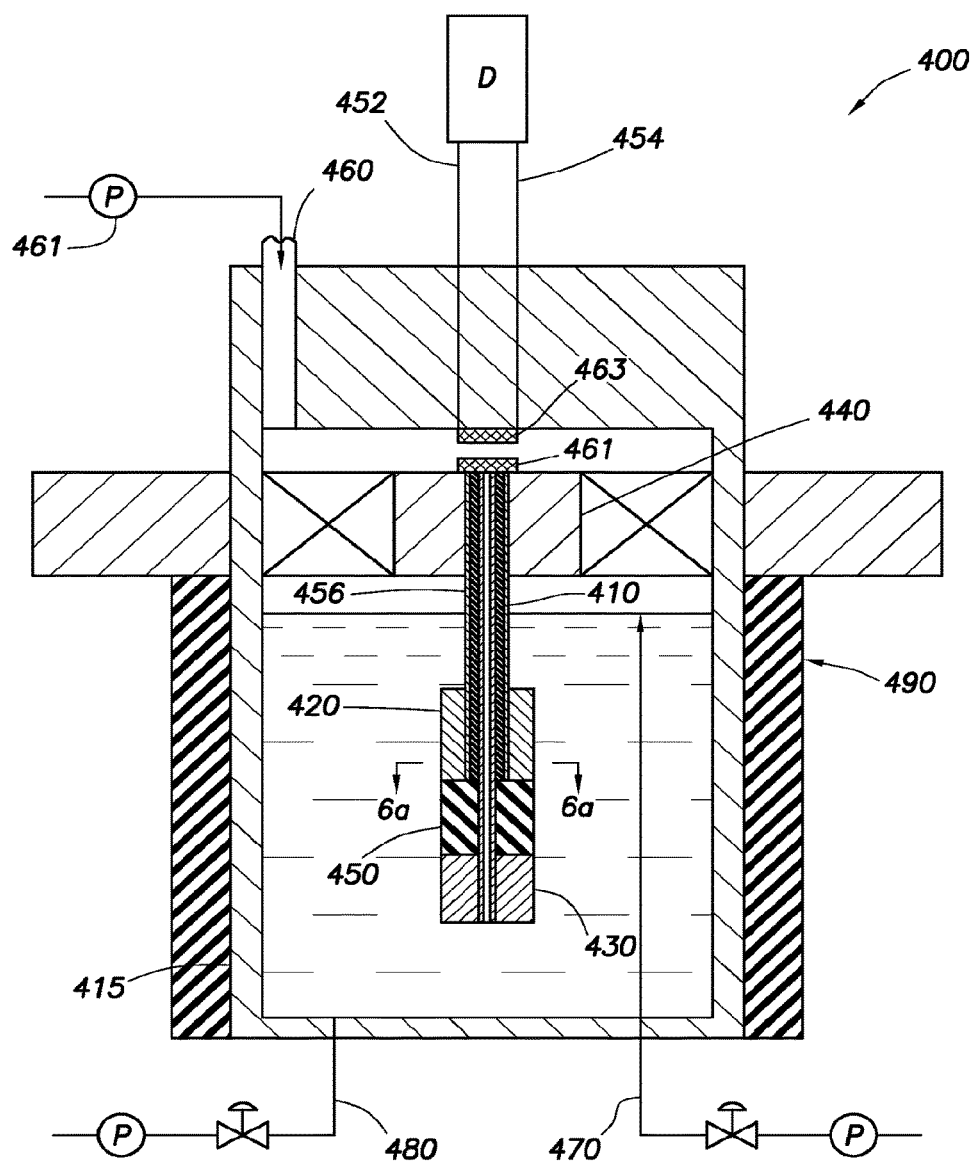
FIG. 6 is a vertical cross-sectional view of an apparatus for measuring the change in surface wetting on a metal surface, which can be selected, for example, to simulate a surface in a well.
Figure 6A:
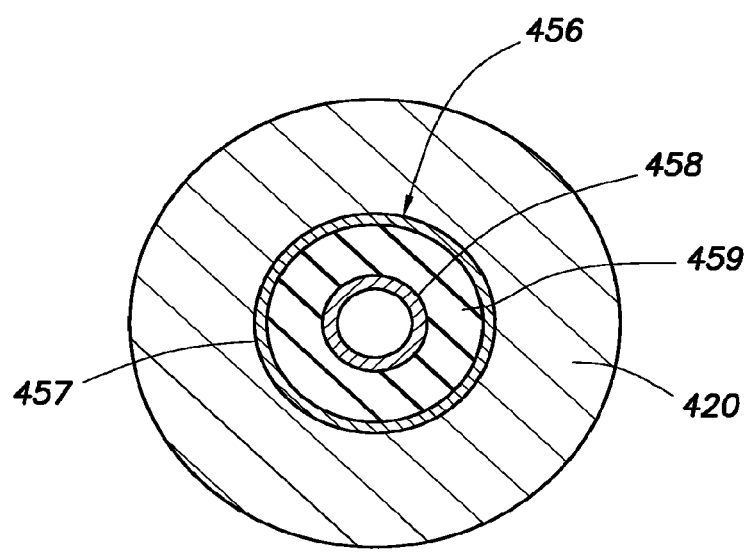
FIG. 6a is a horizontal section illustrating the shape and placement of the concentric shafts and electrode in a test bob.

According to an even further embodiment for simulating downhole conditions on a metallic surface, an electrical system 400 is schematically represented, in FIGS. 6 and 6a. As shown in FIGS. 6 and 6a, the electrical system 400 includes: a bob assembly 410 comprising an electrically insulated electrode holder, a first electrode 420; a second electrode 430, a drive unit 440 all mounted in container 415. The drive unit 440 provides rotational speed R to the bob assembly 410 for shearing a fluid F in the container 415. The drive unit 440 comprises a magnetic motor using electromagnetic forces created outside the container 415 to rotate the bob 410. In addition a torque sensing assembly, such as, disclosed in U.S. Pat. No. 8,347,693 (which is incorporated herein for all purposes) can be provided in the containers 115, 215, 315 or 415 to measure other characteristics of the fluid F, such as apparent viscosity.

Each of the first and second electrodes 420 and 430 comprise cylindrical shaped sections mounted to rotate with the bob 410 as described with respect to FIG. 4. It is envisioned that the bob 410 could alternatively be configured as describe in FIG. 5. As illustrated in FIG. 6a, the shaft 456 of bob assembly 410 comprises concentric shafts 457 and 458 separated by insulator 459. Shafts 457 and 458 are connected respectively to electrodes 420 and 430. Coil 461 can be mounted stationary or to rotate with bob 410. Wires 452 and 454 are operatively connected to the electrodes 420 and 430 through an inductance coil pair and to an EIS measuring device D.

The container 415 in this system comprises a sealed pressure vessel capable of withstanding internal pressures in the range of those present in subterranean well pressures. Container 415 includes a pressurization port 460. The test fluid F can be tested in the container 415 at pressure ranges, for example, from atmospheric to 12,000 psi. Container 415 can also have at least one additional port 470 for adding and/or removing test fluids when the pressurization port is not used for that purpose. Additional ports 480 can also be present located different levels in the container 415. By using the ports 470 and 480 test fluid F can be changed continuously or intermittently during wettability testing by dosing another test fluid that displaces the original fluid under controlled hydrodynamic conditions.

A heater and insulating jacket 490 can also be provided around the container 415 to perform wettability testing at elevated temperatures simulating subterranean wellbore conditions. In this manner testing can be performed with the test fluid F at elevated temperatures as high as 350° F.

This system 400 is adapted for simulating and measuring the formation and/or removal of any wetting or coating or film on the surfaces the electrodes 420 or 430 in the presence of a test fluid F. The changes can be measured under shearing conditions applied to the test fluid F in the system 400 which replicate those present in the well. The composition of the test fluid F can be kept constant during a testing procedure or it can be changed continuously or intermittently by dosing another test fluid that displaces the original fluid under controlled hydrodynamic conditions. In general, the system and applied voltage is adapted such that the electrical circuit is directed across the electrodes 420 and 430 through the test fluid F.

One or both the electrodes 420 and 430 can be used to simulate a downhole metallic or formation material, such as a steal tubular, the test conditions of shear, and optionally temperature and pressure can be adapted to simulate downhole conditions adjacent a downhole materials, and the test fluid can be used to simulate a well fluid in a wellbore. In general, the system 400 can be used, as described herein, to measure any changes in any surface wetting or film on the test electrodes under such simulated test conditions and with such test fluids.

The system 400 is adapted for performing the methods described with respect to FIGS. 3, 4 and 5.

Selecting First Electrode for Downhole Surface to be Simulated

The first electrode is preferably made of the same metallic material as a downhole material, such as a metal tubular, for which any change of water wettability or wetting is to be simulated and determined. The surface of the first electrode can be modified by roughening, polishing, mill varnishing, etc., or it can be a corroded piece of the material, depending on the condition of the downhole tubular to be simulated. The first electrode can be made initially water wetted or oil wetted as desired, to simulate the condition of a downhole surface.

Selecting Second Electrode

The second electrode can be the same as the first electrode, in which case standardization in the experimental method would compel that the first electrode and second electrode be made from the same piece of stock to ensure the same averaged characteristics on both the electrodes. Alternatively, the second electrode can be made from a different material. In addition a non-corrosive conductive material could be used to form the second electrode, such as platinum or graphite, as a standard material. For the ability to compare between labs and companies, it would be preferable to use standard materials as the counter electrode and have an option to use specific well materials if desired. Using standard platinum or graphite electrodes as the counter electrode would eliminate the need to change both the electrodes for testing different materials.

In another embodiment, one or more of the electrodes can be formed from one or more of: the tubular material, the formation material, or a material that can act as a standard.

Preferably, the surface area, aspect ratio, and surface to volume ratio of each of the first and second electrodes is as close as practical to each other for symmetry in the electrical test system.

Selecting Test Fluid

The test fluid can be selected to simulate a well fluid or downhole fluid.

For example, when a water-based spacer fluid is used to displace an oil-based drilling fluid (also known as an oil-based drilling mud) in the annulus prior to pumping cement, a concentration gradient can be clearly noticed at the interface of the spacer fluid and drilling fluid. This concentration gradient is due to mass and momentum transport owing to the differences in densities and rheologies of the bordering fluids, and is better known in the industry by various names, such as intermixing, channeling, and fingering.

A surfactant package of one or more surfactant chemicals is usually included in the water-based spacer fluid to make a stable, water-external emulsion when the water-based fluid mixes with an oil-based fluid, such as an oil-based drilling mud. The surfactant package can include, for example, a combination of: (a) oil-soluble surfactant; (b) water-soluble surfactant; and (c) emulsifier. Surfactants are believed to make the emulsion water external and oil internal.

People skilled in the art of designing cement jobs would appreciate that achieving water wet surfaces downhole is a tradeoff between the surfactant concentrations and contact volumes and concentrations. An initial spacer/mud volume ratio needs to be fixed and the surfactant pack optimization is carried out at that fixed ratio.

Previous methods discuss optimizing the surfactant package by testing to achieve full conductivity in the emulsion. When the conductivity of the emulsion remained constant at all shear rates and equal to that of the pure water-based spacer fluid, it was concluded that the emulsion was a stable emulsion and would not invert back to become unstable. This measures the solution resistivity at only a single frequency, typically 50 Hz or 60 Hz, whichever frequency is locally available. This only gives information on the conductivity of the solution alone, but does not give any information about any interfacial phenomena.

Blending of two phases in the of a fluid system under the effect of shear does not complete cleaning on surfaces. For correct design of operational parameters and fluid systems to meet the design intent of achieving complete surface wetting, it is critical to simulate the shear rates and wall shear rates in an experimental setup at the laboratory scale or via pilot testing to be nominally equivalent to the shear rates expected to be experienced downhole.

Interfacial tension of oil-water phases is reduced by fit-for-purpose surface-active agents under shear causes emulsion to be inverted, thereby changing the continuous external phase from oil to water or vice-versa. US Statutory Invention Registration H1932, dated Jan. 2, 2001, entitled "Wettability and Fluid Displacement in a Well." which is incorporated herein by reference in its entirety, discusses methods and apparatuses used for measuring this phenomena by measuring a property related to the electrical conductivity of the emulsion during the inversion process. A drastic change in electrical conductivity is observed when the inversion occurs. The apparatus consists of a blender jar with a blade at the bottom and electrodes that are built into the jar to measure electrical conductivity. However, the deficiencies of that disclosure include: (1) shear rate profiles and distribution are not similar to the wellbore; (2) shear rates are not quantifiable; (3) resolution of the apparatus is not fine enough to capture differences in conductivity with varying percentage of water wetting on the electrodes; (4) electrodes are contact pins that have very low surface area compared to the mixing geometry; (5) the property being measured is a property and not a surface property; and (6) formation surfaces are not adequately simulated because only small metal pins act as electrodes.

For example, a problem with the US H1932 is that although there are two electrodes in the test cup that are insulated from the cup, the cup is made of metal. Accordingly, in one embodiment the container is made from, coated with or lined with not conductive material.

According to the present disclosure, methods and apparatuses are provided that overcomes the challenges associated existing techniques that include: (1) quantifiable shear; (2) HPHT conditions; (3) workability with particle lade or dirty fluids; (4) ability to study the effect of contact time; (5) additional capability to study how much wall shear stress is needed to overcome the surface tension/cohesion/adhesion effects associated with non-polar surface films. These findings can then be applied to job design for determining fluid properties and operational parameters like pump rates and contact times.

To replicate the downhole conditions and to carry out meaningful testing, a concentration ratio needs to be first fixed and hence, the electrolyte is chosen to be a mixture of an oil-based well fluid and a water-based well fluid in the desired concentration. The water-based well fluid can have a known concentration of surfactant package already pre-mixed.

A coating (layer of oil based mud, filter cake, silicate coating, etc.) whose dielectric properties are different from that of the fluid used (inverter fluid or spacer) for cleaning the coating may be pre-applied and the electrolyte can be the pure, uncontaminated inverter or spacer fluid to simulate the flow behavior in the annulus below the diffuse layer. FIGS. 3a-3b, 4, 5-5a, and 6-6a show schematic representation of various electrical systems where a film can be applied to a surface and subjected to shear by another fluid for the purposes of measuring changes in wetting on the surface.

Alternately, the fluid that is responsible for creating the coating (drilling mud) may be replaced completely with a wash, spacer or inverter fluid while going through an optional process of generating homogenous admixtures with incremental variation on the volumetric ratios between both the fluids. The electrical properties associated with this setup can be monitored to understand the displacement and the dynamics of coating removal. FIGS. 6a-6b, 7, 8, and 9 show the schematic representation of electrical systems where the non-aqueous material will be displaced by a water-wetting wash/spacer/inverter-fluid, while facilitating the application of shear and impedance measurement simultaneously.

Impedance Spectroscopy and Modeling

An alternating current electrical potential difference is applied in between the first and second electrodes and the alternating current flowing in between them is measured. The potential difference needs to be at least sufficient to form a measurable electrical circuit through a fluid between the first and second electrode.

The ratio of the voltage to alternating current flowing across the first and second electrodes is termed as impedance. Unlike resistance, which is a simple linear quotient between voltage and current, impedance is a complex number. When this voltage is alternating in nature, and is applied at various frequencies in the range of 1 microHertz to 1 gigaHertz, and the current responses to these frequencies are measured at the respective frequencies, impedances can be calculated in the frequency domain to give crucial information about bulk, interfacial, and electro-kinetic processes in the system.

With increase in surface water wetting, when such a model is used, it is expected that the values of double layer capacitance and capacitance used to model the non-polar layer will sharply increase due to increasing efficiency of polarization and appearance of opposite charges near the electrode. The value of polarization resistance and charge transfer resistance is expected to decrease sharply.

The value of the solution resistivity is expected to remain constant from the point any mixture of a water-based fluid and an oil-based fluid forms an emulsion that becomes completely water external while other parameters change during the course of the surface wetting operation. If the electrolyte is changed by forming admixtures with incremental concentration levels during the process of displacing one fluid with the other, all parameters are expected to change—therefore a "control experiment" needs to be carried out to determine the electrical parameters of a system with no coating and pure fluid in place. The values derived during the course of the experiments will then need to be compared with the control experiment in order to determine whether a fully wet surface with a well fluid has been achieved. It should be understood that the well fluid can be, for example, a pure a wash fluid, an inverter fluid, a spacer fluid, or a lead cement composition.

The magnitude of the frequency directly relates to the time scale of species and charge transport. As an example, the transport of mass and charge correspond to time scales of $10^{-6}$ sec and are therefore inferred at high frequencies. It can be seen that corrosion, which is a "long term" process, can be predicted at low frequencies that correspond to time scales of the order of 1000 seconds.

For example, when the technique is used with cement slurry electrolyte, the high frequency response (kHz-MHz) may be used to infer conclusions about the parameters like conductivity, diffusivity, and permeability of the cement paste. The intermediate frequency (Hz-kHz) data may be analyzed to provide information about the nature of the near interface zone and the formation of any porous diffuse layer (oxide/carbonate film, etc.) on the first electrode. The low frequency response (mHz-Hz) provides information on the passive behavior of the steel and corrosion related electro-kinetic reactions.

Additional Embodiments of Methods and Apparatuses

According to an embodiment of the disclosure, a method is provided, wherein the method includes the steps of:
 (A) selecting a test material for a surface to be wetted;
 (B) selecting a test fluid;
 (C) testing a system of the test material and the test fluid by moving the test material in the test fluid and using impedance spectroscopy to determine the surface wettability or wetting of the test material with the test fluid under conditions that simulate downhole well conditions.

The testing can be conducted at any convenient location, including in a remote laboratory or in the field at or near the well site.

According to another embodiment the material selecting and moving steps comprise selecting two test materials insulated from each other.

More particularly according to another embodiment of the disclosure, a method is provided including the steps of: provided including the steps of:
 (A) obtaining or providing an apparatus comprising:
  (i) a container forming a chamber;
  (ii) a first surface exposed to or in the chamber, wherein the first surface is of a first electrode, or
  (iii) a second surface exposed to or in the chamber, wherein the second surface is a second electrode;
 wherein the first surface is electrically insulated from the second surface;
 (B) wetting at least the first surface with a first liquid phase of a first fluid;
 (C) after the step of wetting, introducing a second fluid into the chamber, wherein the second fluid comprises a second liquid phase, and wherein the second liquid phase is immiscible with the first liquid phase;
 (D) moving the first and second surface in the second fluid to apply shear between the second fluid in the chamber and the first and second surfaces; and
 (E) making an electrical impedance spectroscopy measurement between the first and second electrode.

According to another embodiment of this method, it includes one or more of the following steps:
 (A) providing an container having a chamber;
 (B) providing first and second electrodes each having a surface;
 (C) insulating the two electrodes;
 (D) placing a first fluid in the chamber;
 (E) replacing the first fluid in the chamber with a second fluid;
 (F) replacing the second fluid with a third fluid;

(G) placing the electrodes in the chamber with their surfaces in contact with the fluid in the chamber;
(H) moving the electrode surfaces while they are in contact with the fluid in the chamber;
(I) replicating subterranean wellbore temperature, pressure and shear conditions in the fluid in the chamber;
(J) making a electrical impedance spectroscopy measurement between the first and second electrodes on the fluids in the chamber;
(K) making a electrical impedance spectroscopy measurement between the first and second electrodes on the fluid in the chamber while moving the electrodes in the fluid;
(L) making a electrical impedance spectroscopy measurement between the first and second electrodes while replacing fluid from the chamber;
(M) comparing electrical impedance spectroscopy measurements to infer differences in the wetting of a electrode surface;

According to an embodiment, the step of taking an electrical impedance spectroscopy measurement includes: operatively connecting an alternating electrical potential source between the first and second electrodes; while operatively connected to the first and second electrodes, varying the electrical potential or the frequency of the alternating electrical potential source; and while varying the electrical potential or the frequency of the alternating electrical potential source, measuring electrical impedance between the first electrode and second electrode to obtain an electrical impedance spectroscopy measurement.

In an embodiment, a surface is oil-wettable. In another embodiment, a surface is water-wettable. The surface can be both oil-wettable and water-wettable, such that wetting with one blocks the surface wettability to another.

In an embodiment, a surface is of a first electrode and the first electrode is selected to be the same material as a metallic tubular used in a well. In another embodiment the electrodes are formed from the same material. In another embodiment the electrodes are formed from different materials.

In an embodiment, a surface is of a first electrode and the first electrode is selected to be the same material as the formation material.

In another embodiment, a surface is of a first dielectric solid material, and wherein the first dielectric solid material comprises a filter cake, a polymeric material, or any combination thereof. In yet another embodiment, the first surface is of the first dielectric solid material and the first dielectric solid material comprises a rock material. The rock material can be or comprise a sedimentary rock. Preferably, the rock material is selected to simulate a downhole subterranean formation in a well. In such an embodiment, the rock can be saturated with the first liquid phase fluid. This could be used, for example, to simulate a rock surface in a well that is wetted with such a liquid phase.

It should be understood that a material of the first surface can be different than a material of the second surface. For example, the first surface can be of the first dielectric solid material and the second surface can be of the second electrode. It should also be understood that a material of the first surface can be the same as a material of the second surface. In another embodiment, the second surface is of the second dielectric solid material and the second dielectric solid material is the same material as the first dielectric solid material.

In an embodiment, the step of wetting with the first liquid phase includes: (i) introducing a first fluid into the chamber, wherein the first fluid comprises the first liquid phase; and (ii) applying a first shear between the first fluid in the chamber and the surfaces.

According to an embodiment, the first liquid phase is a dielectric. According to another embodiment, the first liquid phase is oleaginous. For example, the first liquid phase can be the oil of an oil-based drilling mud used in a well.

According to an embodiment, the second liquid phase has a dielectric constant at least 10% different from the dielectric constant of the first liquid phase.

According to an embodiment, the second liquid phase includes water. In this embodiment, the second liquid phase preferably includes an electrolyte. In an embodiment, the second liquid phase is the continuous phase of the second fluid. In yet another embodiment, the second fluid can be an emulsion of the first liquid phase and the second liquid phase. For example, the second fluid can be an oil-in-water emulsion.

In an embodiment, the second fluid includes various other components. For example, in an embodiment, the second fluid includes a surfactant. In an embodiment, the second fluid can include a solid particulate. The solid particulate can help remove a prior film on the first surface by abrasive action during shearing between the first surface and the second fluid. In another embodiment, the second fluid includes a chemical leaching agent for attacking the first dielectric solid material. In yet another embodiment, the second fluid is a foam. For example, the fluid can be foamed or energized with nitrogen gas.

In an embodiment, the second fluid is a spacer fluid for use in a well. The composition of the second fluid can be changed during shear to simulate fingering, mixing, or channeling during the introducing of such a well fluid into a well.

In an embodiment of the methods, the change in voltage of the alternating electric potential source is in a pseudo linear range. It should be understood that a pseudo linear range means that if $V_1$ gives $I_1$ and $V_2$ gives $I_2$, then $V_1+V_2$ should give $I_1+I_2$.

In an embodiment, the methods additionally include the step of: controlling the temperature of the second fluid in the chamber. For example, the step of controlling the temperature of the second fluid in the chamber can include controlling the temperature to be the design temperature for a well fluid in a well. It should be understood that controlling the temperature can include heating the fluid while in the chamber.

In an embodiment, the methods can additionally include the step of: controlling the pressure of the second fluid in the chamber. For example, the step of controlling the pressure of the second fluid in the chamber can include controlling the pressure to be the design pressure for a well fluid in a well. It should be understood that controlling the pressure can include pressurizing the fluid while in the chamber.

In an embodiment, the step of inferring comprises assuming an equivalent electrical circuit model for the first electrical impedance spectroscopy and second electrical impedance spectroscopy to match experimental impedance changes using non-linear regression techniques.

Preferably, the wetting of first surface is determined as a percentage of the surface that is water-wetted or oil-wetted. For example, the wetting of the first surface in the fluid is determined as a percentage of the first surface that is water wet at: (a) the beginning of the contact time at the contact shear of the fluid; and (b) the end of the contact time at the contact shear of the fluid.

According to an embodiment, the design conditions of introducing the first well fluid into the well include any one of the following: design volume, design shear, design temperature, design pressure, and design pumping time.

In an embodiment, the test fluid is a water-based fluid. For example, the test fluid can be an oil-in-water emulsion. In an embodiment, the oil-in-water emulsion simulates a downhole fluid that results from the mixing of a prior oil-based drilling mud with a spacer fluid that is for changing the wetting of downhole tubular surfaces from oil-wetted to water-wetted before cementing.

In an embodiment where the test material is selected for being similar in substance to a substance of a solid surface in a well, the test fluid is selected for having the design composition of a downhole fluid to be contacted with the solid surface in the well. For example, the downhole fluid is a water-based fluid, such as an oil-in-water emulsion. In some applications, the downhole fluid is a water-in-oil emulsion.

In an embodiment, the system is tested under similar design conditions as the solid surface in the well and the downhole fluid, including at least the design conditions of temperature, fluid contact shear, and fluid contact time at the fluid contact shear. Where the system of the test material and the test fluid is tested under similar downhole conditions as the solid surface in the well and the downhole fluid, the method preferably additionally includes at least the design condition of fluid contact pressure. In an embodiment, the wettability or wetting of the test material in the test fluid is determined as a percentage of the surface that is water-wetted or oil-wetted. Other parameters can additionally be simulated, such as well fluid volume and downhole mixing with another fluid. Preferably, the wetting of the test material in the test fluid is determined as a percentage of the surface that is water wet or oil wet at: (a) the beginning of the fluid contact time at the fluid contact shear; and (b) the end of the fluid contact time at the fluid contact shear.

In an additional embodiment, wetting of the test material is compared at intermediate fluid compositions made with predetermined concentrations of a first oil based fluid, a second water based fluid spacer/wash/inverter-fluid/lead cement slurry with the "control wetting" of the surfaces with the pure second water based fluid. It can be appreciated that the first fluid may be water based and the second fluid may be oil based as the situation demands during the well operations.

In another additional embodiment, the efficiency of the erosion or removal of the coating generated by a first fluid by the second fluid can be measured at predetermined intermediate concentrations of the first fluid and the second fluid under controlled hydrodynamic conditions under the influence of pressure and temperature. The electrical properties associated with this process are recorded dynamically to compare with the control properties with no coating in place and just the second fluid in the system.

The focus of the technique is to understand the contact time and shear rate requirements under pressure and temperature for approaching the wetting values of the test material in contact with the control pure fluid that is deployed for the cleanout operation under pressure and temperature. Wettability or wetting are surface characteristics and may be related to impedance, double layer capacitance, polarization resistance, or charge transfer resistance as accordingly modeled by a relevant equivalent electrical circuit.

In another embodiment, the method can additionally include the step of adjusting or optimizing the design composition of the downhole fluid to be contacted with the solid surface in the well based on the wettability or wetting of the test material in the test fluid.

In an embodiment, the method can further include a step of introducing a well fluid into the well, wherein the well fluid and conditions of introducing are adapted to achieve a downhole fluid and conditions of contacting the solid surface in the well to achieve a design wettability or wetting of the solid surface in the well.

The disclosure provides an opportunity to carry out measurements using a non-invasive technique and quantify water- or oil-wettability or wetting at in-situ conditions. With continuous injection of surfactants and homogenization in the cell, using a mixing paddle, capacitances, and resistances can be monitored with respect to a control fluid to confirm the desired water wettability or wetting.

The methods can be used in surfactant package optimization to render water wet surfaces at downhole conditions.

In some applications, the methods can be used to provide increased probability of achieving full cement shear bond strength and better correlation with cement bond logs.

Prior lab testing using this technique and job execution in the field as designed can decrease the probability of micro annulus development and loss of interfacial bond during the lifecycle of the well and hence improves long-term zonal isolation.

This process can be carried out at HPHT by varying the type of formation or tubular surface experienced downhole, varying surface roughness, mill varnished, polished, corroded, etc.

Therefore, the present disclosure is well adapted to attain the ends and advantages mentioned as well as those that are inherent therein.

The particular embodiments disclosed above are illustrative only, as the present disclosure may be modified and practiced in different but equivalent manners apparent to those skilled in the art having the benefit of the teachings herein. It is, therefore, evident that the particular illustrative embodiments disclosed above may be altered or modified and all such variations are considered within the scope and spirit of the present disclosure.

The various elements or steps according to the disclosed elements or steps can be combined advantageously or practiced together in various combinations or sub-combinations of elements or sequences of steps to increase the efficiency and benefits that can be obtained from the disclosure.

The disclosure illustratively disclosed herein suitably may be practiced in the absence of any element or step that is not specifically disclosed or claimed.

Furthermore, no limitations are intended to the details of construction, composition, design, or steps herein shown, other than as described in the claims.

What is claimed is:

1. A method comprising the steps of:
   a. providing a first and second electrodes each having a surface thereon;
   b. wetting the surfaces on the first and second electrodes with a first fluid;
   c immersing the surfaces on the first and second electrodes in a second fluid;
   d. moving the first and second electrodes in the second fluid; and
   e. at least once during or after applying the moving step, making an electrical impedance spectroscopy measurement between the first and second electrodes while maintaining the electrodes electrically insulated from each other and immersed in the second fluid.

2. The method according to claim 1, wherein the moving step creates shear between the surfaces and the second fluid.

3. The method according to claim 1, wherein the providing, wetting, immersing, moving a measurement steps are performed at one or more of temperatures elevated above atmospheric temperature and pressures elevated above atmospheric pressure.

4. The method according to claim 1, wherein the moving step comprises rotating the first and second electrodes in the second fluid.

5. The method according to claim 1, additionally comprising the steps of: before the moving step, making a first electrical impedance spectroscopy measurement between the first and second electrode; during or after the moving step, making a second electrical impedance spectroscopy measurement between the first and second electrode; comparing the first electrical impedance spectroscopy measurement to the second electrical impedance spectroscopy measurement; and based on the step of comparing, inferring any changes in the wetting of the first surface.

6. The method according to claim 1, wherein the providing, wetting, immersing, moving a measurement steps are performed in a chamber.

7. The method according to claim 6, additionally comprising at least one of the steps of:
controlling the temperature of the second fluid in the chamber, wherein the step of controlling the temperature of the second fluid in the chamber comprises controlling the temperature to be the design temperature for a well fluid in a well; and
controlling the pressure of the second fluid in the chamber, wherein the step of controlling the pressure of the second fluid in the chamber comprises controlling the pressure to be the design pressure for a well fluid in a well.

8. The method according to claim 6, wherein the step of wetting comprises:
a. introducing the first fluid into the chamber; and
b. performing the moving step while the first and second surfaces are immersed in the first fluid in the chamber.

9. The method according to claim 1, wherein the second fluid comprises any mixture of the first fluid and the second liquid phase.

10. The method according to claim 1, wherein the second fluid comprises at least one of water, a surfactant, and a cement composition.

* * * * *